Figure 1:
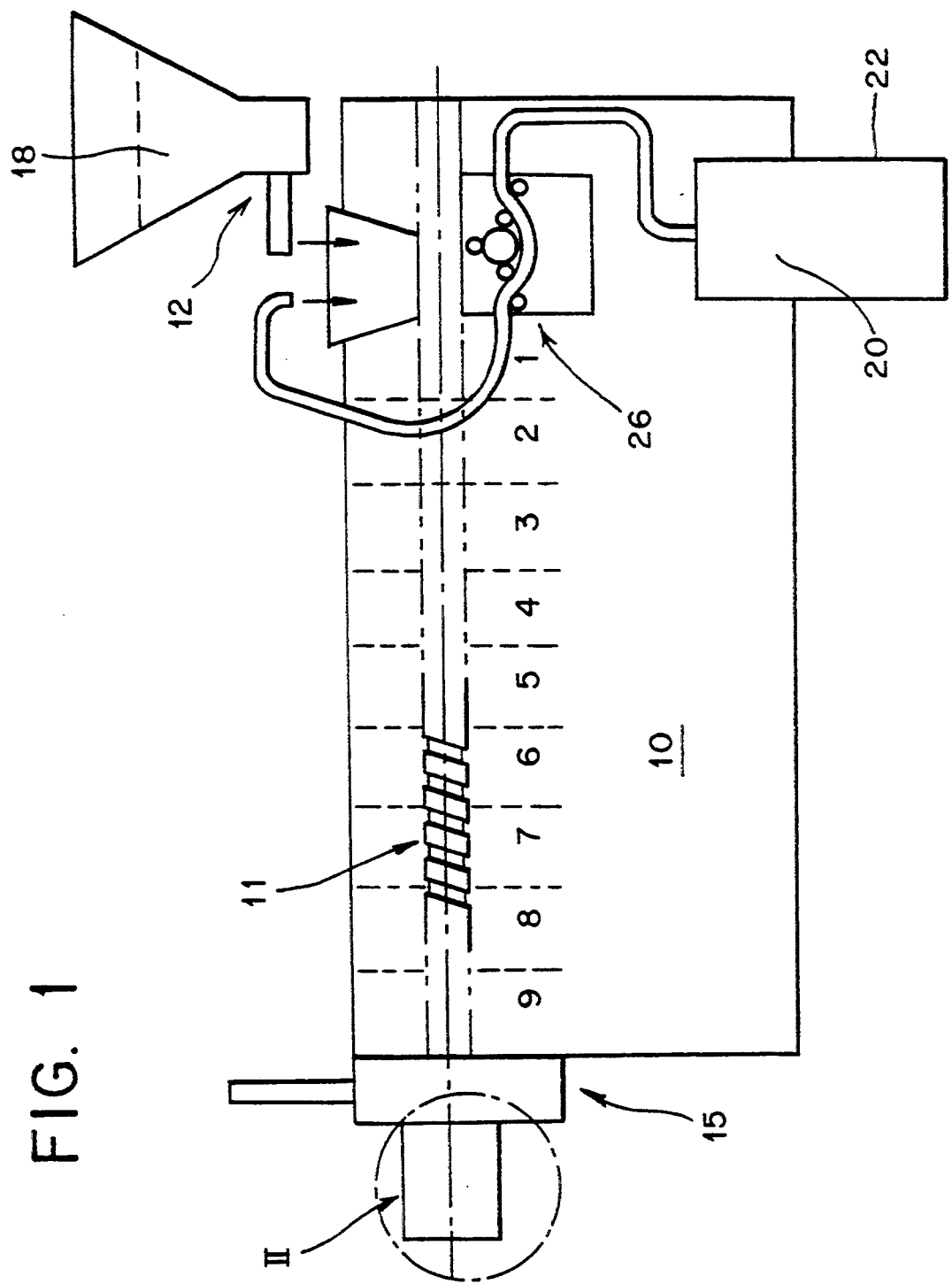
Figure 2:
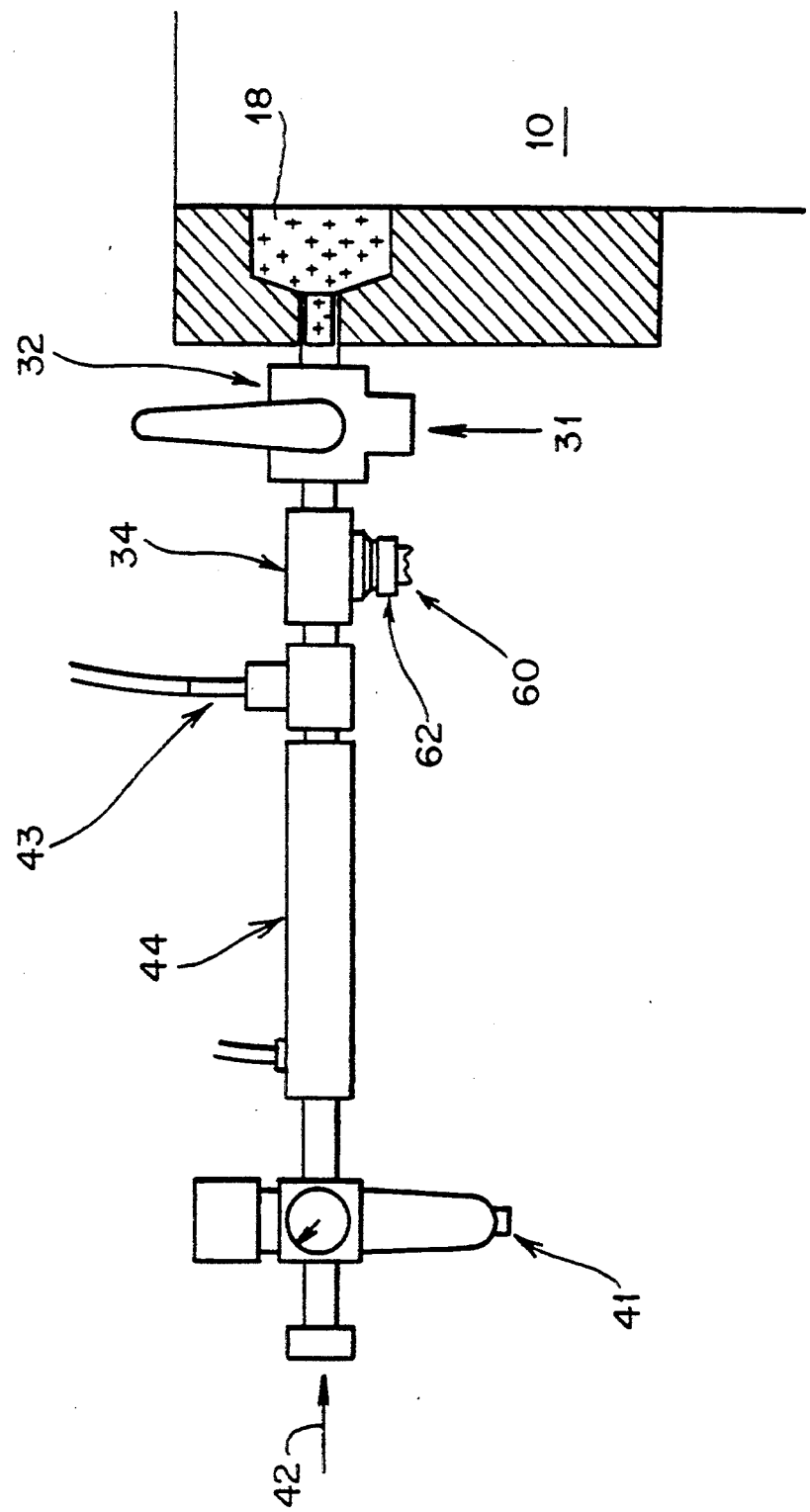

United States Patent [19]

Bogue et al.

[11] Patent Number: 5,380,473
[45] Date of Patent: Jan. 10, 1995

[54] PROCESS FOR MAKING SHEARFORM MATRIX

[75] Inventors: B. Arlie Bogue, Broad Run; Richard C. Fuisz, Great Falls, both of Va.; Peter G. Hiscocks, Saffron Walden, England

[73] Assignee: Fuisz Technologies Ltd., Chantilly, Va.

[21] Appl. No.: 965,804
[22] Filed: Oct. 23, 1992
[51] Int. Cl.$^6$ .................................................. B29B 9/10
[52] U.S. Cl. .................................... 264/11; 264/12; 264/13; 425/6; 425/7
[58] Field of Search ............... 264/11, 12, 13; 425/6, 425/7

[56] References Cited

U.S. PATENT DOCUMENTS

| | | |
|---|---|---|
| 2,826,169 | 3/1958 | Le Veen . |
| 2,918,404 | 12/1959 | Mende et al. . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,131,428 | 5/1964 | Mika . |
| 3,231,639 | 1/1966 | Mabru ........................... 425/7 |
| 3,308,221 | 3/1967 | Opfell . |
| 3,324,061 | 6/1967 | Tanquary et al. . |
| 3,557,717 | 1/1971 | Chivers . |
| 3,595,675 | 7/1971 | Ash et al. . |
| 3,615,671 | 10/1971 | Schoaf . |
| 3,625,214 | 12/1971 | Higuchi . |
| 3,723,134 | 3/1973 | Chivers . |
| 3,762,846 | 10/1973 | Chivers ......................... 425/7 |
| 3,856,443 | 12/1974 | Salvi ............................. 425/9 |
| 3,875,300 | 4/1975 | Homm et al. . |
| 3,925,525 | 12/1975 | LaNieve . |
| 3,930,043 | 12/1975 | Warning et al. ............. 426/515 |
| 3,951,821 | 4/1976 | Davidson . |
| 3,967,623 | 7/1976 | Butterworth et al. . |
| 3,972,725 | 8/1976 | Nicol . |
| 3,992,265 | 11/1976 | Hansen . |
| 4,090,920 | 5/1978 | Studer, Jr. . |
| 4,136,145 | 1/1979 | Fuchs et al. ................. 264/164 |
| 4,153,512 | 5/1979 | Messner et al. . |
| 4,293,570 | 10/1981 | Vadasz ........................... 426/3 |
| 4,303,684 | 12/1981 | Pitchon et al. ............... 426/312 |
| 4,371,516 | 2/1983 | Gregory et al. ............... 424/485 |
| 4,376,743 | 3/1983 | Dees ............................. 264/103 |
| 4,492,685 | 1/1985 | Keith et al. . |
| 4,496,592 | 1/1985 | Kuwahara et al. .............. 426/5 |
| 4,500,546 | 2/1989 | Turbak et al. ................. 514/781 |
| 4,526,525 | 7/1985 | Oiso et al. ..................... 425/9 |
| 4,585,797 | 4/1986 | Cioca ........................... 514/773 |
| 4,619,833 | 10/1986 | Anderson ...................... 426/548 |
| 4,692,371 | 9/1987 | Morman et al. ................ 264/12 |
| 4,793,782 | 12/1988 | Sullivan ......................... 425/7 |
| 4,855,326 | 8/1989 | Fuisz ........................... 514/777 |
| 4,873,085 | 10/1989 | Fuisz ........................... 424/400 |
| 4,885,281 | 12/1989 | Hanstein et al. ................ 514/53 |
| 4,923,646 | 5/1990 | Kinsley, Jr. .................... 264/13 |
| 4,978,537 | 12/1990 | Song .............................. 426/5 |
| 4,997,856 | 3/1991 | Fuisz . |
| 5,011,532 | 4/1991 | Fuisz ........................... 106/215 |
| 5,028,632 | 7/1991 | Fuisz ........................... 514/772 |
| 5,034,421 | 7/1991 | Fuisz ........................... 514/772 |
| 5,096,492 | 3/1992 | Fuisz ........................... 106/215 |
| 5,114,631 | 5/1992 | Nyssen et al. ................... 264/6 |

FOREIGN PATENT DOCUMENTS

| | | |
|---|---|---|
| WO91/18613 | 12/1991 | European Pat. Off. . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |

OTHER PUBLICATIONS

Massoud Kazamzadeh, Ph.D., *Food Process Design Developing Product Through Extrusion* (Jul. 1992).

*Primary Examiner*—Mary Lynn Theisen
*Attorney, Agent, or Firm*—Hoffmann & Baron

[57] ABSTRACT

The present invention is a unique process and apparatus for making a new matrix material called a shearform matrix which results in transformation of the morphology of a feedstock. The process is characterized by increasing the temperature of a nonsolubilized feedstock carrier to a point where it will undergo internal flow, followed by ejecting a stream of the feedstock and then subjecting it to disruptive fluid shear force which separates it into separate parts or masses which have a transformed morphology. The shearform matrix may include other ingredients such as oleaginous material and actives.

28 Claims, 5 Drawing Sheets

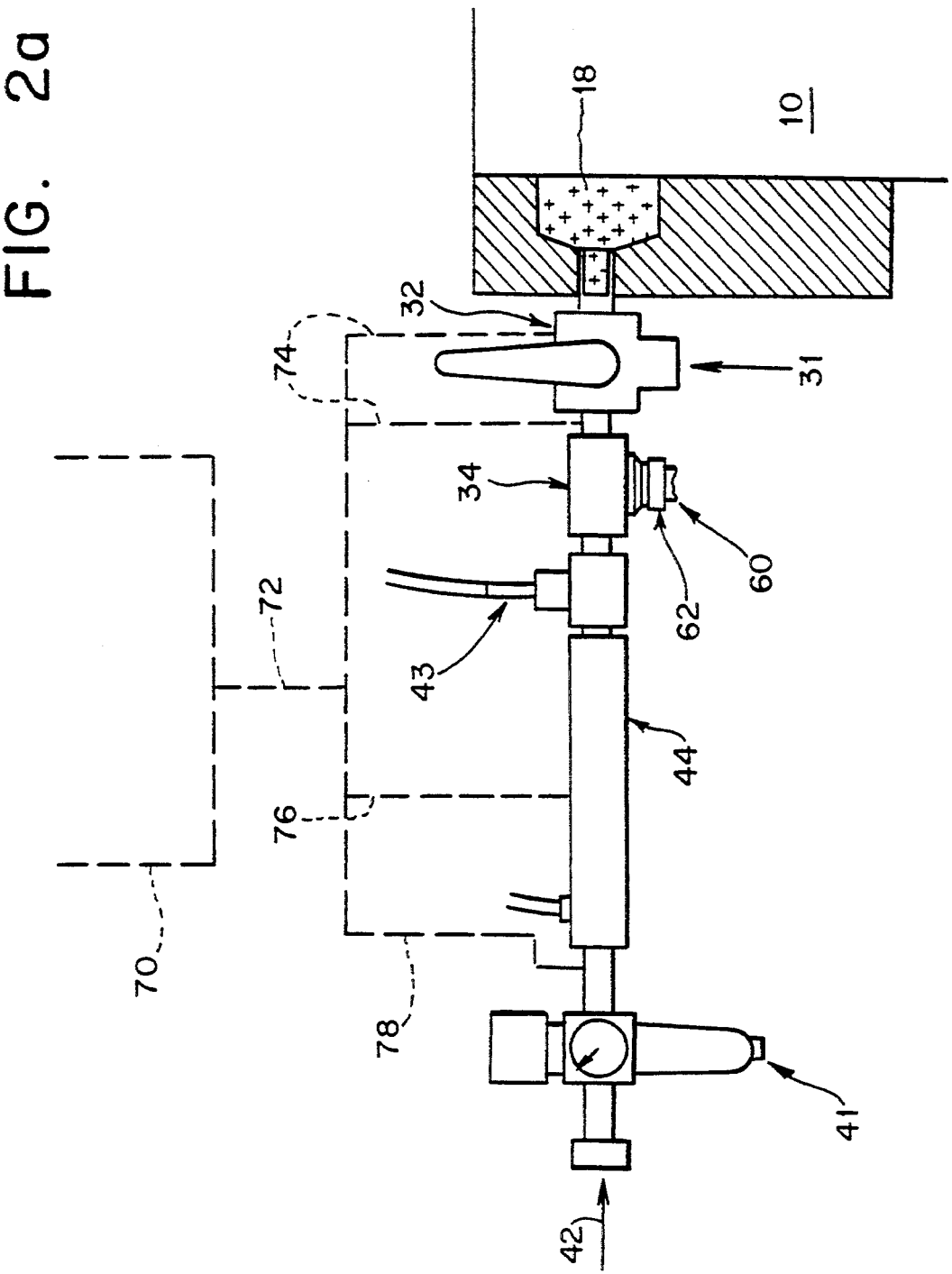

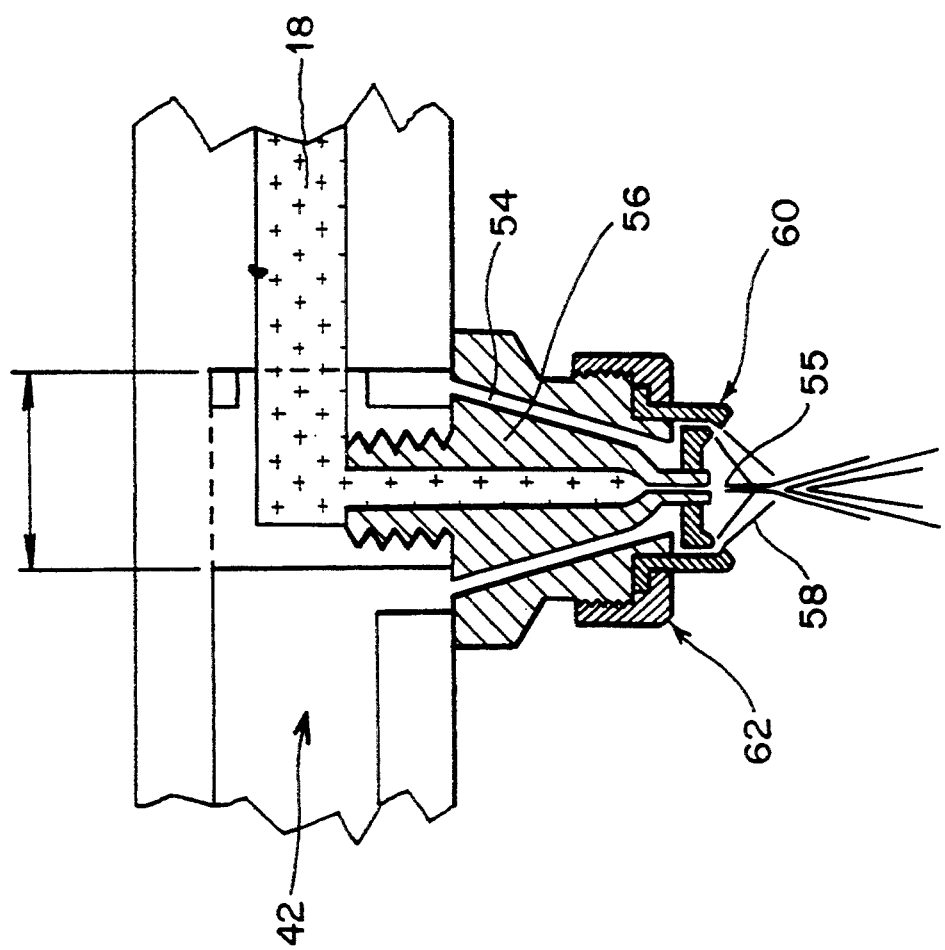

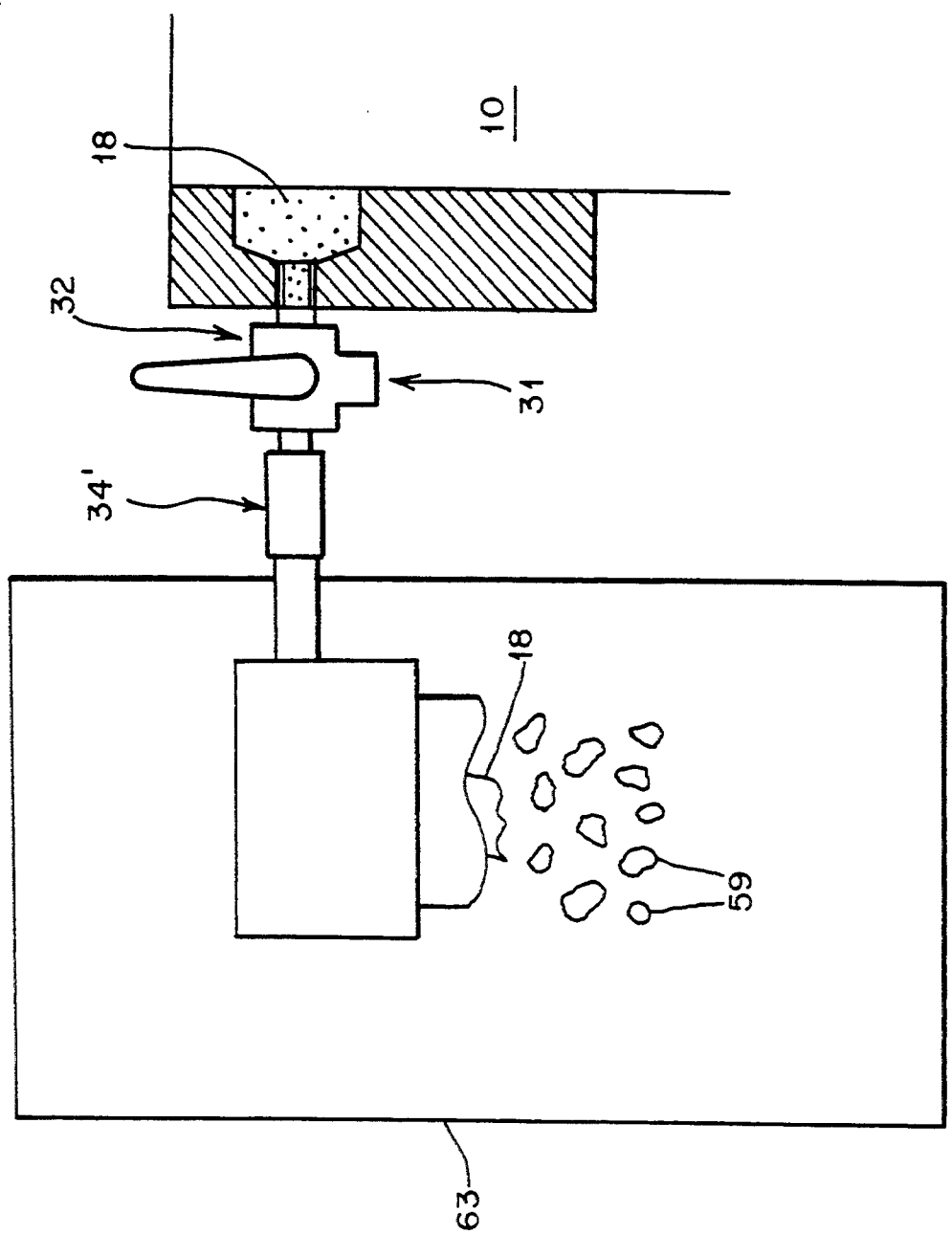

PROCESS FOR MAKING SHEARFORM MATRIX

BACKGROUND OF THE INVENTION

The present invention relates to a unique process and apparatus for making a new matrix material resulting from transformation of the morphology of feedstock material.

The art of material processing has developed significantly in recent years. Increased awareness of the impact that different substances have on the environment and on the species found therein has fostered a virtual explosion of technology for providing alternative forms of material. Well-known substances have been subjected to close scrutiny to discover clean, efficient, and controlled methods of handling and exposing them to the world. It is also important to develop new forms of material for application in various fields.

One area of material processing includes technology which relates to the reduction of material structure by use of heat during processing. Processing food and food ingredients many times includes such technology.

For example, a series of U.S. patents issued to Thomas E. Chivers (U.S. Pat. No. 3,762,846, U.S. Pat. No. 3,723,134, and U.S. Pat. No. 3,557,717) disclose a solution process for making candy floss from a cooked slurry or syrup. The ingredients are blended and heated at a first temperature, e.g., 200°-205° F. (93°-96° C.), to form a slurry. After forming the slurry, the batch is cooked or boiled at a substantially higher temperature, e.g., about 340° F. (171.1° C.), and thereafter discharged through an atomizing nozzle. Most of the moisture contained in the molten candy flashes off as it is discharged. The Chivers disclosures rely on dissolution of the ingredients, e.g., sugar and other ingredients, in water and then heating extensively to drive the water from the solution. Most of the water is driven off after discharging the solution. Thus, the Chivers technology suffers from drawbacks associated with sustained high temperature processing and dissolution of ingredients during processing.

Another method for process material is disclosed in European Patent Application 0 387 950 A1 of Stork. The Stork process is a method of preparing a foam spray-dried product by collision of a stream of gas which contains dry particulate material, with a jet of droplets of a liquid solution. A liquid solution which contains at least one of the ingredients of the end product is combined with gas and heated before spraying as a jet of droplets for collision with the dry particulate. The Stork system is designed to process a low density product; it requires an elaborate equipment arrangement, and is energy intensive.

UK Patent Specification G B 2 155 934 B of Shukla, et al. discloses a method for crystallizing sucrose or glucose from a solution. Shukla, et al. subject a sugar solution to evaporation to produce a supersaturated sugar solution. The supersaturated solution is then subjected to shear in a continuous screw extruder to induce nucleation. The retention time of the syrup is below 25 seconds (on the average) at a temperature of 115° C. to 145° C. (239° F.–293° F.) for sucrose and 100° C.–135° C. (215° F.–275° F.) for glucose. After the syrup is subjected to progressive nucleation, Shukla, et al. pass the syrup onto a moving band to permit crystallization to continue at a gradual rate at relatively high temperature. The Shukla, et al. process requires maintenance of the solution at temperatures which do not drop below the boiling point of water.

Other disclosures include British Patent Specification No. 1 460 614 and U.S. Pat. No. 3,972,725 (Tate & Lyle Limited) which disclose a continuous process wherein a syrup solution is catastrophically nucleated and discharged into a crystallization zone. Catastrophic nucleation is achieved by subjecting the solution to shear force which can be applied in an apparatus such as a colloid mill or homogenizer. The solution is discharged onto a moving band where the water must be boiled off by maintaining the material at a relatively high temperature. A related process has been disclosed in British Patent Specification 2 070 015 B and U.S. Pat. No. 4,342,603, which is used for crystallization of glucose. In the disclosed procedure, a supersaturated solution is subjected to shear force and allowed to crystallize on a belt. Both the sucrose process and the glucose process require solution processing at high temperatures and are, consequently, energy intensive.

U.S. Pat. No. 3,365,331 to Miller, U.S. Pat. No. 4,338,350 and U.S. Pat. No. 4,362,757 describe a process for crystallizing sugar, which involves impact beating a sugar solution to provide nucleation. The process involves input of considerable amount of energy and has problems directly related to temperature control.

U.S. Pat. No. 3,197,338 to Hurst, et al. discloses a process for crystallizing glucose which includes kneading a glucose solution to induce nucleation followed by crystallization to form a solid glass which is then ground. Another glucose crystallization process has been disclosed in GB 2 077 270 B in which starch hydrolyzate is concentrated by evaporation and then simultaneously crushed and mixed during crystallization while cooling. The product is further milled. These processes also require nucleating by beating a solution which includes glucose.

More recently, technology for material processing has been disclosed by Dr. Richard C. Fuisz. In U.S. Pat. No. 4,855,326 various substances having pharmological properties were combined with sugar and spun to produce a readily water-soluble product. Other disclosures which relate to spinning substances with one or more sugars are found in U.S. Pat. No. 4,873,085, U.S. Pat. No., 5,034,421, U.S. Pat. No. 4,997,856 and U.S. Pat. No. 5,028,632. U.S. Pat. No. 5,034,421 to Fuisz discloses spun matrix systems containing medicaments having predetermined release patterns.

The examples in the Fuisz disclosures set forth above describe processing feedstock material by subjecting it to high speed spinning on a spinning head in which the substance is also subjected to heating against a heating element. The change of temperature is quite large, which is believed to be occasioned by the spinning head quickly and efficiently spreading the feedstock material against the heating element circumferentially disposed around the perimeter of the spinning head. Thus, extensive surface contact of the feedstock is provided against the heating element itself while being spun.

The feedstock material is heated sufficiently to create an internal flow condition which permits part of the feedstock to move at a subparticle level with respect to the rest of the mass and exit openings provided in the perimeter of the spinning head. The centrifugal force created in the spinning head flings the flowing feedstock material outwardly from the head so that it reforms with a changed structure. The force required to separate and discharge flowable feedstock is only the centrifugal force which results from the spinning head. These examples describe one approach to producing a novel matrix material.

It is an object of the present invention to overcome drawbacks which are associated with the non-Fuisz procedures. It is also an object of the present invention to provide improvements over the technology previously disclosed and claimed by Dr. Fuisz.

SUMMARY OF THE INVENTION

The present invention is a unique process and apparatus for making a shearform matrix by raising the temperature of a feedstock material which includes a non-solubilized carrier to a point where the carrier undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted in accordance with the present invention to continue in a free-flow condition until solidified. Accordingly, conditions are provided at the point of shear whereby the feedstock is maintained in a free-flow condition until the new masses are beyond the shearing step.

Ideally the temperature of gas is controlled when used as the shear-producing fluid. The temperature is controlled to provide a gas temperature which is at least 0.1° C. greater than the flow point temperature of material being ejected for each atmosphere of pressure of gas applied against said material as a shear force. Thus, if there are 10 atmospheres of pressure applied, the temperature of gas should be at least 1° C. greater than the temperature of the material being ejected. This feature has been found to optimize the shearing effect and maintain the ejected feedstock in free-flow condition until it is separated and has traveled beyond the shear step.

The feedstock material used in the present process is one which includes a carrier selected from the group consisting of saccharide-based materials, thermoplastic polymers, biodegradable polymers and cellulosics. Preferably the feedstock material is organic, that is most compounds of carbon. Basically, the feedstock is selected for use herein based on the ability to be processed without reliance upon dissolution. The feedstock material may contain minor amounts of material which is dissolved, but the processability of the feedstock relies on a carrier capable of undergoing internal flow without the necessity of dissolution. In the case of saccharide-based materials, the feedstock is primarily a solid material which is subjected to the process.

The term saccharide-based materials includes sugars and sugar derivatives. Sugars are referred to in a classical sense which means sucrose, maltose, fructose, lactose, glucose, arabinose, xylose, galactose, et al. Sugar alcohols are also included in the term sugars. A non-limiting list of sugar alcohols includes the following: sorbitol, mannitol, maltitol, pentatol, isomalt (Palatinit ®), xylitol, et al. Sugar derivatives include chemical and enzymatic derivatives and includes, but is not limited to, chloro derivatives of sugar such as sucralose.

Saccharide-based materials can have varying degrees of low-monomer saccharides, or sugars, oligomers, and polysaccharides, such as starch. Some saccharide-based materials are prepared by hydrolysis of starch and are classified by the degree of starch polymer hydrolysis. The measuring unit is referred to as D.E. or dextrose equivalent. D.E. is defined as reducing sugars expressed as dextrose and reported as a percentage of the dry substance.

A saccharide-based material having high short-carbon-chain content, e.g., glucose and low-unit oligomers thereof, usually results in a higher dextrose equivalent, (D.E.). However, saccharide-based material having greater long-carbon-chain content, e.g. high monomer unit oligomers and polymers usually results in a lower D.E. rating.

For example, maltodextrins contain a mix of sugars and polysaccharides which range from long-chain oligomers resulting from starch hydrolysis to sugars having a low number of monomeric units. Under FDA guidelines maltodextrin consists of nonsweet, nutritive saccharide polymers having a D.E. of less than 20, while corn syrup solids is regarded by the FDA as having a D.E. greater than 20. The present inventors, however, refer to maltodextrins collectively as saccharide-based material consisting of nonsweet, nutritive saccharide polymers and other oligomers having six-carbon monomer units which collectively provide a carrier material capable of forming a matrix. In all uses, the carrier material in the present invention is non-solubilized.

In a preferred embodiment of the present invention, other materials can be included in the feedstock. For example, oleaginous material can be included in the feedstock which, among other things, can act as a crystallization-control agent. By crystallization-control agent is meant that the matrix which is formed as a result of the present process and apparatus can be in an amorphous condition and subjected to an environment in which it will crystallize in a controlled manner. Other hydrophobics may be used as a control for crystallization and are contemplated to be part of the present invention. Some of the oleaginous materials which are contemplated for use in the present invention are as follows: vegetable oils, soy bean oil, canola oil, corn oil, cocoa butter, sunflower oil, animal fats, tallows, lards, fish oils, crustacean oils, and mixtures thereof.

The feedstock can also contain an additive selected from the group consisting of bioeffecting agents, dyes, fragrances, crystallization control agents, sweeteners, flavors, and mixtures thereof. A non-limiting list of bioeffecting agents is as follows: antitussives, antihistamines, decongestants, alkaloids, mineral supplements, laxatives, vitamins, antacids, ion exchange resins, anticholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, antipsychotics, antitumor drugs, anticoagulants, antitnrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

Since a number of bio-affecting agents are heat sensitive, the present invention includes a process step of introducing heat sensitive agents at a point sufficiently proximal the ejection step to reduce exposure of the heat sensitive to prolonged heat conditions. Thus, any heat sensitive agent can De incorporated into a carrier for subsequent ejection and formation of a shearform matrix product.

In order to implement the unique process, an apparatus is provided which has a means for increasing the temperature of a non-solubilized feedstock and simultaneously increasing the applied pressure on the feedstock to advance it for ejection. Preferably, this means for increasing and advancing the feedstock can be a multiple heating zone twin screw extruder. Preferably there are greater than four (4) zones, and in the present preferred mode there are nine (9) zones.

The second element: of the apparatus is a means for ejecting the feedstock in a condition for shearing it to provide the shearform matrix- The means for ejecting is in fluid communication with the means for increasing the temperature and pressure and is arranged at a point to receive the feedstock while it is in the internal flow condition. Preferably this means for ejecting the feedstock is a nozzle which provides high pressure ejection of the feedstock material. In order to maintain the free-flow condition of the matrix beyond the point of shear, it is preferable to include temperature-maintenance means throughout the means for ejecting.

In a preferred embodiment, the apparatus can also include a port for introducing an additive or agent to the carrier at a point close enough to ejection to prevent or minimize degradation of the agent. In this way heat sensitive agents can be introduced without fear of losing their activity—e.g., bio-affecting properties.

Finally, the apparatus includes a means for shearing the feedstock which is arranged proximally to the ejector and is disposed to effect shear of the feedstock while it is in the internal flow condition. Preferable the means for shearing is a means for delivering fluid such as air at high velocity against the feedstock stream as it exits a nozzle. Such a device can be an external atomizing nozzle. In one embodiment the air provided for shearing can be heated to enhance the free-flow of the separated masses beyond the point of shear.

In an alternative embodiment, the means for shearing can be a chamber in which the environment can be maintained to induce shear upon the collision of a high velocity stream of feedstock directed against the preselected and maintained environment. Generally, the temperature and humidity of the shearing environment is maintained at a level which induces shear in feedstock (having internal flow) directed against this environment at high velocity.

As a result of the present invention dry emulsions based on material capable of breaking down at high temperatures can be prepared. The process is highly controllable and is able to produce high volumes of shearform matrix with tight control of temperatures and/or low high-heat residence times which minimize degradation of the feedstock or feedstock additives.

The present invention has been shown to provide a shearform product which has a more amorphous structure, e.g., more random, than a product prepared from a solution process. The resulting matrix is capable of dispersing more oil in water than with spun product. This is demonstrated by greater tyndall effect. Thus, a maltodextrin having a given D.E. will disperse a greater amount of oil as a shearform product than as a spun product. This is believed to be the result of producing a greater number of finer particles which carry oil than can be produced by spinning. Also a much more stable dispersion can be established. In order to separate oil from a dispersion created with a shearform matrix ether or hexane is required whereas heat and centrifugation is generally suitable for separating oil from a dispersion resulting from a spun matrix.

Other and further improvements which the present invention provides over the prior art will be identified as a result of the following description which sets forth the preferred embodiment of the present invention. The description is not in any way intended to limit the scope of the present invention, but rather only to provide a working example of the present preferred embodiments. The scope of the present invention will be pointed out in the appended claims.

BRIEF DESCRIPTION OF THE DRAWINGS

Preferred embodiments of the invention have been chosen for the purposes of illustration and description and are shown in the accompanying drawings, wherein:

FIG. 1 is a schematic of the overall process and apparatus with the shear region detailed in FIGS. 2 and 3;

FIG. 2 is a detailed schematic of the encircled shear region II of FIG. 1; and

FIG. 2*a* is a schematic as shown in FIG. 2 with phantom lines depicting a preferred embodiment which provides introduction of an additive without prolonged heating; and FIG. 3 is yet a further detail schematic of the preferred ejection arrangement for the preferred embodiment of the present invention.

FIG. 4 is a schematic depicting a high velocity nozzle and an environment-maintenance chamber as means for shearing feedstock.

DETAILED DESCRIPTION OF THE INVENTION

A shearform matrix according to the present invention is a matrix formed by transformation of a feedstock having a carrier material which has a structure capable of being altered by heating. The feedstock material is heated sufficiently to permit transformation of the morphology of the carrier when it is subjected to a disruptive shear force. The condition at which the disruption occurs is referred to herein as internal flow. Internal flow contemplates the ability of the material to move and separate at subparticle level sufficiently to cause discontinuity in the feedstock. In the context of the present invention the disruptive force is applied to the stream of feedstock rather abruptly over a very short period of time so that the duration of the force can be considered instantaneous.

The inventors have found that in a presently preferred embodiment of the invention, the feedstock can be subjected to a stream of fluid, gas or liquid, impacting the feedstock at a velocity which creates the flash disruptive shear force. The force created by fluid impinging against the feedstock is referred to as disruptive fluid shear force.

Presently, the preferred fluid is air. However, the invention is not limited to the type of fluid used to create the disruptive fluid shear force.

In one embodiment air is directed against the feedstock as a continuous high velocity jet. Another embodiment contemplates propelling the feedstock at high velocity against the force of an air atmosphere. In both cases the feedstock is abruptly disrupted into discrete discontinuous masses due to shear acting on the feedstock material while it has internal flow.

Another characteristic of the shearform matrix of the present invention is a morphology which results from allowing flash-disrupted feedstock to reform during free flow transformation from its original morphology. This unique free-flow transformation is achieved by preventing hindrance of continued flow while the material cools to a new matrix structure.

In order to provide the new matrix material of the present invention, a unique apparatus has been devised which is able to deliver the feedstock to a point where it is subjected to shear while in the internal flow condition. The unique apparatus has several features which make it uniquely adept for this process.

Referring to FIG. 1, a twin screw extruder 10 provides the chamber in which the feedstock material is heated. Heating is controlled in the series of heating zones 1–9.

The feedstock 18 is fed into the chamber from hopper/feed 12 in non-solubilized condition. By non-solubilized in the present invention is meant that the ingredients have not been subjected to dissolution for purposes of processing. A small amount of water (or other agents) may be used as a processing aid to ensure smooth flow, and assist generally in the advancement of the throughput. These processing aids are not provided, however, to change the nature of the feedstock from non-solubilized to solubilized.

The multiple-zone twin screw extruder has been used to effect controlled heating and feeding. The multiple zones are used to heat the feedstock sufficiently to attain a temperature at which internal flow occurs. Inasmuch as the temperature is increased inherently as a result of friction occurring during mixing and displacement with most feedstock materials externally supplied temperature can be reduced to a certain extent to accommodate the autologous temperature produced during extrusion. In the examples which follow, extrusion was performed using a APV Baker MPF50 twin-screw co-rotating extruder with an L:D ratio of 25 to 1. Nine zones were provided for applying controlled heating between input and exit. Screw configurations can be adjusted to meet the requirements of the process.

An important factor in the present invention is to heat and extrude feedstock to attain a condition at which internal flow is possible without going substantially beyond such point or creating an extended residence time in the extruder. This balance is achieved by selecting proper machine size, adjusting volume of throughput, selecting the optimum screw design and heating at the separate zones to ensure that internal flow condition is met but not exceeded. Consequently, as soon as the proper condition is achieved, the extrusion is terminated by passing the feedstock through an ejection means such as a nozzle.

In the first set of experiments which are described hereinafter, sugar was processed as the carrier material and the balance of temperature and time as explained in the preceding paragraph was satisfied by providing a nine-zone temperature profile and advancement speed set forth in Table I. Consequently, the sugar feedstock did not reside in the final three zones, i.e., Zones 7, 8 and 9, for more than about 90 seconds.

In the second set of experiments, maltodextrin was used as the carrier material in the feedstock and was processed using a temperature profile and advancement speed set forth in Table II to achieve the temperature and time requirements. As a result the maltodextrin feedstock did not reside in the final three zones, Zones 7, 8 and 9, for more than about 90 seconds.

In both cases, the feedstock was heated and advanced at a rate which provided internal flow conditions without substantially heating beyond such point and with minimum residence time under such conditions. Overextension of either temperature or time results in deterioration of the carrier as well as creating of a non-processable mass of feedstock.

Additional ingredients 20, such as oleaginous material can be stored in reservoir 22 and metered into the feedstock by a pump 26. The mixing, pressurizing and advancing elements are shown schematically as screw 11. A head clamp or adaptor plate 15 has also been provided to direct the throughput of feedstock from the extruder to the shearing portion of the apparatus designated by circle II. A detailed depiction of this region is provided in FIG. 2.

Referring to FIG. 2, the ejection portion of the apparatus and process is schematically depicted. Specifically, feedstock 18 is derived from extruder 10 under pressure and permitted to advance by use of a valve mechanism 32. Preferably a 3 port valve is used to direct the extruded mass to an alternate outlet such as port 31 if required. Immediately downstream of the valve mechanism is a high pressure nozzle 34.

In the present preferred embodiment, the nozzle is a high pressure, low velocity nozzle which extrudes a substantially coherent stream of feedstock. In an alternative embodiment, the nozzle can be a high velocity nozzle which extrudes the feedstock under high pressure and at high velocity.

Referring again to FIG. 2, in the present preferred embodiment shear is provided to the feedstock material while in the internal flow condition by directing a stream of high velocity air against the coherent stream exiting the nozzle. The high velocity air can be provided by air stream 42 which can pass through a filter and pressure/flow regulator 41 to am in-line heater 44 and a thermo-couple 43 to control the temperature of the air. The in-line heater 44 can be used to raise the temperature of the air to enhance the free-flow feature of the sheared masses separated from the feedstock stream. Preferably, the air is heated to a temperature of about 130° C. to about 210° C. for sucrose and from about 85° C. to about 180° C. for maltodextrins.

FIG. **2*a* depicts another embodiment which provides the ability to inject an additive to the feedstock at a point where it will not degrade before being ejected. It is known that some ingredients, especially bio-affecting active ingredients, are heat sensitive and will deteriorate in the presence of prolonged heat condition. The present invention solves this problem by including an additive dispensing vessel 70 from which an additive can be drawn along feedline 72. The new ingredient can then be added along any one of injection ports 74, 76, and 78. Static mixers between 31 and 34 will achieve greater mixing efficiency when the ingredient is added at port 74. It should be understood that the present invention is not limited to the configuration shown in FIG. 20**. Injection ports can be provided at any point in the process and apparatus described herein. The skilled artisan can select the desired configuration depending on the lability of the additive and the characteristics of the apparatus used.

The stream of air is directed against the feedstock exterior by the nozzle to provide discontinuities in the feedstock and basically transform the morphology of the original feedstock to a new morphology achieved by free-flow solidification as discontinuous masses. Referring to FIG. 3, air stream 42 is seen as being in fluid communication with annular channel 54 which surrounds the internal nozzle device 56. Feedstock 18 is shown being fed to the nozzle and exiting as a coherent stream 55 where it is subjected to high-velocity air stream 58 which is created by the combination of tortuous path exits provided by air cap 60 and retaining ring 62.

Other measures can be taken to ensure that the internal flow condition created in the extruder/heater is not lost by heat transfer as the processed feedstock is advanced to the point of shear and beyond to permit free-flow reformation. For example, valve mechanism 32 can be heated to eliminate transfer of heat from the feedstock to a relatively cooler valve mechanism. Moreover, heat can be maintained at the point of shear, generally identified by elements 60 and 62, by directing a heatgun at them during operation or by using a temperature controlled heating band. Alternatively, the temperature of the internal nozzle 56 can be raised or lowered relative to a stream of heated air to prevent transfer of heat from the feedstock and consequent cooling below flow conditions. As the process continues, however, a steady-state temperature of each of the mechanisms will be attained so that additional heat to individual elements of the operations is not required to prevent undue heat transfer and cooling.

When air is used to create the shear force, it is applied in a two-fluid nozzle at a pressure of from about 1.5 to about 20 atmospheres. Preferably, the pressure is applied at about 2 atmospheres to 10 atmospheres. As previously mentioned, the temperature of the air used to create the shear force should preferably be controlled to a temperature at least about 0.1° C. above the temperature of the feedstock being ejected for every atmosphere of pressure.

In each of the Examples which follow shear force was applied through a two-fluid nozzle, shown in FIG. 3, by air fed at a pressure of about 3 atmospheres. The temperature of the air was maintained before exiting the nozzle at about 185° C. for sucrose and at about 150° C. for maltodextrin. When the pressure of the air at the nozzle shown at FIG. 3 is 2 atmospheres, the velocity of the air impinging on the stream of feedstock is 68 feet per second, and when the pressure is 4 atmospheres, the velocity of air is 95 feet per second.

The unique process and apparatus disclosed herein will be further explained and exemplified in actual experiments, the results of which are set forth hereinbelow. These examples, however, are not meant to limit the scope of the present invention.

EXAMPLES

Experiments have been run which test the premises of the present invention in actual use. The object was to determine whether or not a transformed shearform matrix could be produced from a non-solubilized feedstock. In order to do so, tests were conducted basically in two phases. The first phase employed a crystalline sugar (sucrose), as the solid feedstock material or carrier. This sugar was fed to the twin screw extruder as described above without solubilized feedstock components. Furthermore, the sugar was processed with an oleaginous material to determine whether or not an oleaginous component could be successfully incorporated as part of the shearform matrix product. The results were surprisingly quite favorable and demonstrate that a continuous process can be employed for production on a commercial scale.

Sugar Examples

In the first experiments, sugar was processed in the extruder at a screw speed of three hundred (300) revolutions per minute. The temperature profile of the extruder as well as the feed rate of the feedstock and processing aid has been set forth in Table 1. It is noted that water was included as a processing aid in the experiments.

TABLE I

| Experiment No. | Sugar Feed Rate (Kg/h) | Oil Feed Rate (Kg/h) | Processing Aid H$_2$O (Kg/h) | Temperature Profile °C. Zones | | | | | | | | |
|---|---|---|---|---|---|---|---|---|---|---|---|---|
| | | | | 1 | 2 | 3 | 4 | 5 | 6 | 7 | 8 | 9 |
| 1 | 36.0 | — | 1.0 | 30 | 50 | 90 | 180 | 180 | 200 | 200 | 200 | 200 |
| 2 | 36.0 | — | 1.0 | 30 | 50 | 90 | 180 | 180 | 200 | 200 | 200 | 200 |
| 3 | 36.0 | 3.6 | 1.0 | 30 | 50 | 90 | 180 | 180 | 200 | 200 | 200 | 200 |
| 4 | 36.0 | 19.6 | 1.0 | 30 | 50 | 90 | 180 | 180 | 200 | 200 | 200 | 200 |
| 5 | 36.0 | 11.8 | 1.0 | 30 | 50 | 90 | 180 | 180 | 200 | 200 | 200 | 200 |

In each of the experiments, sucrose in the form of crystalline sugar was used as the dry feed. The temperatures shown in Table I start from the first zone (the zone closest to the inlet hopper of the extruder) through the ninth zone (the last zone adjacent to the exit). The feed was ejected from the nozzle under a pressure of about 500 psig, e.g., about 34 atmospheres.

Experiment No. 1

In the first experiment the product which was obtained using sucrose alone with a trace amount of water as a processing aid had an excellent appearance. The shearform matrix was substantially white in color and had a white cotton wool texture. This material was easily adaptable for many uses in which the new shearform product would be considered applicable.

Experiment No. 2

In the second run the conditions were similar to those of the first experiment.. The product again appeared as a floss but had a slightly darker color than the relatively unadulterated white appearing product of run number 1.

Experiment No. 3

In Experiment No. 3, the conditions were the same as Experiments No. 1 and 2, except that oil was added to the feed to determine whether or not the shearform matrix would be able to accommodate an additional ingredient such as an oleaginous material. In particular canola oil was introduced at a rate of 3.6 kilograms per hour. Otherwise the conditions were kept the same as in the previous two experiments. The product obtained was a white, opaque cotton-like shearform matrix which was acceptable in appearance and texture.

Experiment No. 4

In the next experiment, Experiment No. 4, the inventors increased the amount of oil to be incorporated in the shearform matrix by about 200%, e.g., from 3.6 Kg/h to 9.6 Kg/h. The remaining conditions were kept the same as in the previous run.

The experiment produced an excellent product, which was clean white in color and cotton-wool-like in texture. This is an excellent product considering that the oil content is approximately 21%. Furthermore, no oil separation whatsoever was detected.

Experiment No. 5

Finally, with respect to the sugar experiments, the oil feed was increased even further to a rate of 11.8 Kg/h for a content of about 24% in the final product. The feedstock processed very nicely under the conditions of the previous experiments and sprayed well from the nozzle into a fluffy material which dispersed readily into the surrounding environment. The product was a beautiful white cotton-wool-like floss material.

While other experiments were conducted to test variables in the processing of the matrix of the feedstock to produce the shearform matrix, it was found that the process and apparatus devised for producing the new shearform product were dependable on a commercial scale. In each of the experiments set forth above the shearform matrix product possessed a morphology which was quite different from the morphology of the sugar carrier in the feedstock.

The sucrose/oil product produced in the above experiments was added to water and produced very fine colloidal dispersions of the oil.

Maltodextrin Examples

Further experiments were performed with other solid feedstock material to evaluate the capabilities of the invention. In particular maltodextrin solids were used to discover whether or not a new shearform matrix could be produced therefrom. The maltodextrin used in the following experiments was Hubinger Dri Sweet 36. The conditions for these experiments are shown on Table II.

Experiment No. 6

Experiment 6 was conducted to determine whether or not a new shearform matrix could be obtained from a solid maltodextrin feedstock without any other components. In order to perform the experiment, maltodextrin was fed at a rate of 25 Kg/h with a processing aid of water fed at a rate of 1.5 Kg/h. The temperature profile is shown on Table II. The feedstock was maintained at a very uniform flow to obtain a thin cotton-like product which was evenly sprayed though the nozzle. The product was satisfactory for use as a shearform matrix.

Experiment No. 7

Experiment No. 6 was run to determine whether or not oleaginous material could be incorporated into the new shearform matrix. Thus, oil was fed in with the feedstock maltodextrin at a rate of about 17% by weight, e.g., 4.1 Kg/h of oil to 20 Kg/h of dry maltodextrin feedstock. The feedstock was advanced at a processing rate of 350 rpm and at a temperature profile as shown in Table II. The result was very white, thin, brittle product which had no visible oil separation. Thus, oleaginous material can be successfully incorporated in a shearform matrix produced from a dry maltodextrin feedstock.

Experiment No. 8

A further experiment was run similar to the conditions of Experiment No. 7, but with a reduced processing speed of 300 rpm. The product was again in the form of very thin white particle product which showed no signs of oil separation.

Experiment No. 9

Further experiments were run to confirm the results of Experiments Nos. 7 and 8. In Experiment No. 9, the maltodextrin was processed with oil the same as set forth in Experiment No. 7 to produce an attractive white thin product which confirms the capability of reproducing a shearform matrix from solid maltodextrin feedstock with oleaginous incorporated therein.

Experiment No. 10

In Experiment No. 10 the solid maltodextrin feedstock was reduced to a rate of 15 Kg/h while the oil content was kept at 4.1 Kg/h. The product prepared in accordance with this experiment would contain a nominal amount of 21.5% oleaginous. The experiment was run under the conditions set forth in Table II and the product obtained was the most attractive of all of the experiments. It had a very low density and a high-quality white appearance. The shape of the product was somewhat fiber-like.

TABLE II

| Experiment No. | Corn Syrup Solids Feed Rate (Kg/h) | Oil Feed Rate (Kg/h) | Processing Aid H$_2$O (Kg/h) | Temperature Profile °C. Zones | | | | | | | | | Screw Speed (rev/min) |
|---|---|---|---|---|---|---|---|---|---|---|---|---|---|
| | | | | 1 | 2 | 3 | 4 | 5 | 6 | 7 | 8 | 9 | |
| 6 | 25 | — | 1.5 | 20 | 40 | 40 | 40 | 40 | 40 | 40 | 65 | 65 | 375 |
| 7 | 20 | 4.1 | — | 20 | 20 | 20 | 40 | 40 | 60 | 60 | 85 | 85 | 350 |
| 8 | 20 | 4.1 | — | 20 | 20 | 20 | 40 | 40 | 60 | 60 | 85 | 85 | 300 |
| 9 | 20 | 4.1 | — | 20 | 20 | 20 | 40 | 40 | 60 | 60 | 85 | 85 | 350 |
| 10 | 15 | 4.1 | — | 20 | 20 | 20 | 40 | 40 | 60 | 60 | 85 | 85 | 350 |
| 11 | 15 | 3.4 | — | 20 | 20 | 20 | 40 | 40 | 60 | 60 | 86 | 100 | 350 |
| 12 | 15 | 3.6 | — | 20 | 20 | 20 | 40 | 40 | 60 | 60 | 85 | 100 | 400 |

Experiment No. 11

In Experiment No. 11 the temperature in the last barrel zone was increased to 100° centigrade and a heating element was installed on the ball valve and a heat gun was directed to the nozzle to ensure that a temperature was maintained so that the product would remain in free-flow condition as it exited and subjected to shear. The results were excellent. In Experiment No. 11 a 19% oleaginous content product was obtained in the form of small, very white spicules with absolutely no bulk phase separation whatsoever in the product.

Experiment No. 12

The results of Experiment No. 11 were confirmed in subsequent experiment at which the production rate was increased by advancing the feedstock under a screw speed of 400 rpm. Once again, the results were excellent in that a very white, small, thin spicule product resulted. Moreover, it was possible to continuously run at the high speed for at least one hour.

As a result of the experiments set forth above, it has been determined that a dry feedstock material can successfully be transformed into a new matrix for applications in many fields of technology.

Another embodiment (shown in FIG. 4) utilizes a single fluid nozzle which ejects feedstock 18' at high pressure and velocity, ejecting feedstock from the nozzle at a velocity sufficient to cause instantaneous disruption of the ejected stream in the ambient atmosphere chamber 63. In a present preferred embodiment it has been found that the velocity necessary to form shearform product can be created by providing a pressure of about 2,000 psi. The pressure will of course vary as nozzle size varies. Central to the process is that stream of feedstock be ejected with sufficient velocity to create the separation of the stream into masses 59 of shearform product.

Thus, while there have been described what are presently believed to be the preferred embodiments of the present invention, those skilled in the art will realize that other and further modifications can be made without departing from the true spirit of the invention, and is intended to include all such modifications and variations as come within the scope of the claims as set forth below.

We claim:

1. A process for making a shearform matrix comprising:

a) controlledly increasing the temperature of a feedstock which includes a solid non-solubilized carrier material capable of undergoing internal flow in the absence of dissolution to a point where said carrier material will undergo internal flow with the application of disruptive fluid shear force;

b) ejecting said heated feedstock resulting from step (a) as a coherent stream under pressure from at least one orifice; and c) then subjecting said coherent stream of feedstock to a disruptive fluid shear force which separates said coherent stream of feedstock into multiple discrete and discontinuous parts and transforms the morphology of said feedstock into said shearform matrix.

2. A process according to claim 1 wherein said multiple parts are cooled to a temperature below said internal flow point immediately after contact with said fluid shear forces and separation of said stream into multiple parts.

3. The process of claim 1 wherein an environment is provided for said multiple parts to reform as solid shearform matrix under conditions which permit free-flow until solidification.

4. The process of claim 1 wherein said carrier material selected from the group consisting of saccharide-based materials, thermoplastic polymers, biodegradable polymers, and cellulosics.

5. The process of claim 4 wherein said feedstock further comprises a crystallization control agent.

6. The process of claim 5 wherein said crystallization control agent is an antihumectant.

7. The process of claim 5 wherein said feedstock comprises an oleaginous material selected from the group consisting of vegetable oils, soy bean oil, canola oil, corn oil, sunflower oil, animal fats, tallows, lards, fish oils, crustacean oils, and mixtures thereof.

8. The process of claim 4 wherein said feedstock further comprises an additive selected from the group consisting of bio-affecting agents, dyes, fragrances, crystallization control agents, sweeteners, flavors, and mixtures thereof.

9. The process of claim 1 wherein said temperature is controlledly increased to said internal flow point in the substantial absence of heating beyond said point and with minimum residence time during said controlled temperature increase.

10. The process of claim 9 wherein said feedstock is simultaneously pressurized.

11. The process of claim 9 wherein said controlled temperature increase is provided by passing said feedstock through a feeder chamber having multiple temperature-control zones.

12. The process of claim 11 wherein said feedstock is passed through said multiple zones under conditions which prevent heating substantially beyond said internal point and which minimizes time in said chamber.

13. The process of claim 4 wherein said fluid shear force results from directing a fluid at high velocity at said stream of extrudate.

14. The process of claim 13 wherein said feedstock is sucrose and said fluid is air maintained at a temperature of from about 160° C. to about 200° C. and ambient atmosphere has a relative humidity of less than 30% RH.

15. The process of claim 13 wherein said feedstock is maltodextrin and said fluid is air maintained at a temperature of from about 85° C. to about 180° C. and ambient atmosphere.

16. The process of claim 4 wherein said fluid shear force results from extruding said feedstock through said nozzle at high velocity against a fluid atmosphere at a condition which provides discrete, discontinuous masses.

17. An apparatus for making a shearform matrix comprising:

means for advancing, and controlledly increasing the temperature of a feedstock which includes a solid non-solubilized carrier material and applied pressure on said solid non-solubilized carrier material to the point where said carrier undergoes internal flow and is simultaneously advanced for ejection;

means for ejecting said feedstock as a coherent stream for shearing said feedstock to provide said shearform matrix, said means for ejecting in a fluid communication with said means for increasing the temperature and pressure and arranged to receive said feedstock material during said internal flow condition; and means for disruptively shearing said feedstock fixed proximally to said means for ejection and disposed for effecting shear of said coherent stream of feedstock during said internal flow condition into multiple discrete and discontinuous masses whereby said feedstock material is transformed to said shearform matrix.

18. The apparatus of claim 17 wherein said means for increasing the temperature comprises a multiple-zone chamber having selectively heatable zones and a continuous throughput mechanism for advancing said feedstock.

19. The apparatus of claim 18 wherein said throughput mechanism comprises at least one screw mechanism for extruding said feedstock.

20. The apparatus of claim 19 wherein said means is a twin screw extruder having at least four heating zones.

21. The apparatus of claim 20 wherein there are nine heating zones.

22. The apparatus of claim 17 wherein said means for ejecting is a high pressure nozzle.

23. The apparatus of claim 22 wherein said nozzle is a low velocity nozzle which provides a substantially coherent stream of said feedstock at an exit orifice.

24. The apparatus of claim 22 wherein said nozzle is a high velocity nozzle having at least one opening for ejecting feedstock at high velocity.

25. The apparatus of claim 17 wherein said means for shearing said feedstock comprises means for delivering fluid for high velocity against feedstock as it exits said means for ejecting.

26. The apparatus of claim 25 wherein said means for delivering fluid comprises an external atomizing nozzle.

27. The apparatus of claim 24 wherein said means for shearing comprises an environment-maintenance chamber which maintains an environment which induces shear upon collision of said high velocity feedstock against said environment.

28. The apparatus of claim 17 wherein said apparatus comprises means for injecting an additive to said feedstock at a point proximal said means for ejecting said feedstock.

* * * * *